United States Patent [19]
Lurie et al.

[11] Patent Number: 5,423,772
[45] Date of Patent: Jun. 13, 1995

[54] CORONARY SINUS CATHETER

[75] Inventors: Keith G. Lurie, Minneapolis; David G. Benditt, Edina; Jeffrey J. Shultz, Robbinsdale; John D. Ockuly; John J. Fleischhacker, both of Minnetonka, all of Minn.

[73] Assignee: Daig Corporation, Minnetonka, Minn.

[21] Appl. No.: 106,383

[22] Filed: Aug. 13, 1993

[51] Int. Cl.6 ............................................. A61M 25/00
[52] U.S. Cl. ................................ 604/282; 604/281; 128/642; 607/122
[58] Field of Search ............... 128/642, 673, 119, 122, 128/123, 125–128; 604/281, 282; 126/656, 658

[56] References Cited

U.S. PATENT DOCUMENTS

| 4,856,529 | 8/1989 | Segal | 128/673 X |
|---|---|---|---|
| 5,215,540 | 6/1993 | Anderhub | 604/281 |
| 5,306,263 | 4/1994 | Voda | 604/281 |

FOREIGN PATENT DOCUMENTS

| 453008 | 10/1991 | European Pat. Off. | 604/281 |
|---|---|---|---|
| 0154801 | 4/1982 | German Dem. Rep. | 607/122 |
| 3704667 | 9/1987 | Germany | 128/642 |

OTHER PUBLICATIONS

"Gorlin Electrode Catheter for Coronary Sinus Studies and Pacing", USCI disclosure, Dec. 1971.
"USCI. Position II ® and Nycore TM Cardiovascular Catheters", pp. 1–21.

Primary Examiner—Lee S. Cohen
Assistant Examiner—Jeffrey R. Jastrzab
Attorney, Agent, or Firm—Scott R. Cox

[57] ABSTRACT

A catheter for insertion in the ostium of the coronary sinus in the right atrium comprised of a main reinforced portion, an intermediate zone portion and a soft tip portion wherein a portion of the catheter is curved in a double curve, wherein the first curve is a first longitudinal curve, wherein the second curve is a second longitudinal curve, wherein the second longitudinal curve is curved in approximately the same direction as the first longitudinal curve and wherein the first and second longitudinal curves are generally coplanar.

13 Claims, 2 Drawing Sheets

| 1 | FOSSA OVALIS |
| --- | --- |
| 2 | CSL CATHETER |
| 3 | I.V.C. |
| 4 | OS of C.S. |
| 5 | TRICUSPID VALVE |
| 6 | EUSTATION RIDGE |
| 7 | S.V.C. |

CORONARY SINUS CATHETER

BACKGROUND OF INVENTION

1. Field of Invention

This invention relates to cardiac catheters, more particularly, this invention relates to a specialized catheter to be used in the coronary sinus of the heart.

2. Prior Art

Catheters have been in use in medical procedures for many years. For example, they can be used to convey an electric stimulus to a selected location within the human body. Further, they can be used to monitor and make measurements for diagnostic tests of activities within the human body. Such catheters examine, diagnose and treat while positioned at a specific location inside the human body which are otherwise inaccessible without more invasive procedures. Recently, catheters have become more commonly used within the human heart and vascular system. In such use, the catheter is first inserted into a major vein or artery which is near the body surface. The catheter is then guided to the area for diagnosis or treatment by manipulating the catheter through the vessels of the body. As the utilization of catheters in remote and difficult to reach portions of the body including the heart has increased, it has become important to control precisely the movement of the catheter.

Control of the movement of catheters is difficult because of the inherent structure of the catheter. The body of conventional catheters is long and tubular. To provide sufficient control over the movement of the catheter, it is necessary that its structure be somewhat rigid. However, the catheters must not be so rigid as to prevent navigation of the catheter through the body vessel to arrive at the precise location where the medical procedure will be performed. In addition, it is imperative that the catheter not be so rigid as to cause damage to the body vessel through which it is being passed.

While it is important that the catheter not be so rigid as to cause injury to vessels and arteries, it is also important that there be sufficient rigidity in the catheter to accommodate torque control, i.e., the ability to transmit a twisting force along the length of the catheter. Sufficient torque control enables controlled maneuverability of the catheter by the application of a twisting force at the proximal end of the catheter that is transmitted along the catheter to its distal end. The feature of existing catheters which provides greater torque control often conflicts with the need for reduced rigidity to prevent injury.

One common method of addressing this problem has been the use of catheters with decreasing levels of rigidity through the length of the catheter, particularly through the use of a "soft" tip at the distal end of the catheter. See, for example, U.S. Pat Nos. 4,385,635, 4,886,506, 5,122,125, 4,563,181, 4,863,442, 4,753,756, 4,636,346 4,898,591 and 4,596,563.

As above stated, catheters are used increasingly for medical procedures involving the human heart. In these procedures, the catheter being used is typically guided to the heart through vessels including arteries, veins, and cardiac chambers and then it is placed at a precise location within the heart. Typically, the catheter is inserted in an artery or vein in the leg, neck, upper chest or arm of the patient and threaded, often with the aid of a guidewire in the catheter, through various arteries and veins until the tip of the catheter reaches the desired location. The distal portion of the catheter may be preformed into a desired curvature so that by torquing the catheter about its longitudinal axis, the catheter can be manipulated to the desired location within the heart. For example, U.S. Pat. No. 4,882,777 discloses a catheter with a complex curve at its distal end for specific procedures in the right ventricle of a human heart. Further, U.S. Pat. No. 4,117,836 discloses a catheter for the selective coronary arteriography of the left coronary artery and U.S. Pat. Nos. 5,016,640 and 4,883,058 disclose catheters for the use in the right coronary artery. In addition, U.S. Pat. No. 4,898,591 discloses a catheter with inner and outer layers containing braided portions. That patent discloses a number of different curvatures of intervascular catheters.

Unfortunately, none of the disclosed products are adequate for use in the coronary sinus of the heart. The coronary sinus is the largest cardiac vein and runs along the atrioventricular groove and empties into the right atrium. Thus, new catheters designed specifically for use within the coronary sinus are necessary.

Accordingly, it is an object of this invention to prepare a catheter designed for ease of access of, and for use in the coronary sinus.

Another object of this invention is to prepare a fixed shaped catheter for use in the coronary sinus which can provide electrophysiological sensing for various locations within the coronary sinus.

It is a still further object of this invention to provide a fixed shape coronary sinus catheter which can sense electrical activity in and/or deliver electric energy to the right and left atria as well as the left ventricle.

These and other objects are obtained by the design of the coronary sinus catheter of the instant invention.

SUMMARY OF INVENTION

The instant invention is a fixed shape catheter for use in the coronary sinus of the human heart comprised of a main reinforced portion, an intermediate zone portion and a softened tip portion, wherein the distal portion of the catheter contains a double curve comprised of a first longitudinal curve with a radius extending through an arc of about 30 to 50 degrees and wherein a second longitudinal curve with a radius extending through an arc of about 45 to about 90 degrees, wherein both the first and second longitudinal curves are curved in the same direction and are generally coplanar.

While the instant catheter is designed for use in the coronary sinus, it is certainly not limited to that application but can be used for other procedures in the heart and in other locations within the body. Further, the catheter's use is certainly not limited to electrophysiological diagnostic applications but can be used for interventional pacing, defibrillation, ablation, cardioversion and other such cardiac procedures.

DETAILED DESCRIPTION OF THE DRAWINGS

A coronary sinus catheter in accordance with this invention is provided for maintaining precise location and continuous electrical contact within the coronary sinus of the heart.

Increasingly, procedures have been designed to investigate, analyze and diagnose the cause of arrhythmias that occur in the heart. In a normal heart contraction and relaxation of the heart muscle takes place as electrochemical signals pass sequentially through the myocardium from the atria to the ventricular tissue along a well defined route including the His-Purkinje System. The signal originates at a site called the sinus node in the right atrium. Methods to diagnose the cause of certain arrhythmias include connection of a patient to patch leads placed on the chest of the patient to record the electrical activity of the heart. These procedures are commonly called electrocardiograms. The record of electrical activity as a function of time is referred to as an "electrogram." However, more specific information with regard to the patient's arrhythmia can be gained by placing diagnostic electrophysiology catheters with sensing electrodes at specific locations in the heart. Once these electrodes are in a predetermined, precise location within the heart, readings can be taken which will help determine the types of arrhythmias and diagnose the problems of the patient's heart. These electrophysiological analysis require the precise placement of the electrophysiological catheter within the heart. Examples of locations for the placement of these catheters include designated points within the right atrium, the right ventricle, near the bundle of the His and, especially when information is desired from the left side of the heart, in the coronary sinus.

The coronary sinus is the largest cardiac vein which serves as a venous conduit from smaller veins within the myocardium to the right atrium. The coronary sinus extends from an opening for the coronary sinus in the right atrium, along the posterior of the heart to the left side of the heart along the atrioventricular border. When an electrophysiology catheter is placed in the coronary sinus, intracardiac electrograms may be obtained from the left atrium as well as the left ventricle if proper contact is made with the designated locations in the heart. In addition, if electrodes are placed on the catheter outside of the coronary sinus, electrograms may be obtained of activity within the right atrium and even from the right ventricle. The location of the electrodes and their size, shape and location on the catheter may vary depending on the needs of the physician and the specific procedures for which the catheter is utilized. Preferably, the electrodes are located from the tip of the catheter up to 20.0 cm., or more proximally, from the tip along the body of the catheter.

Figure 1:
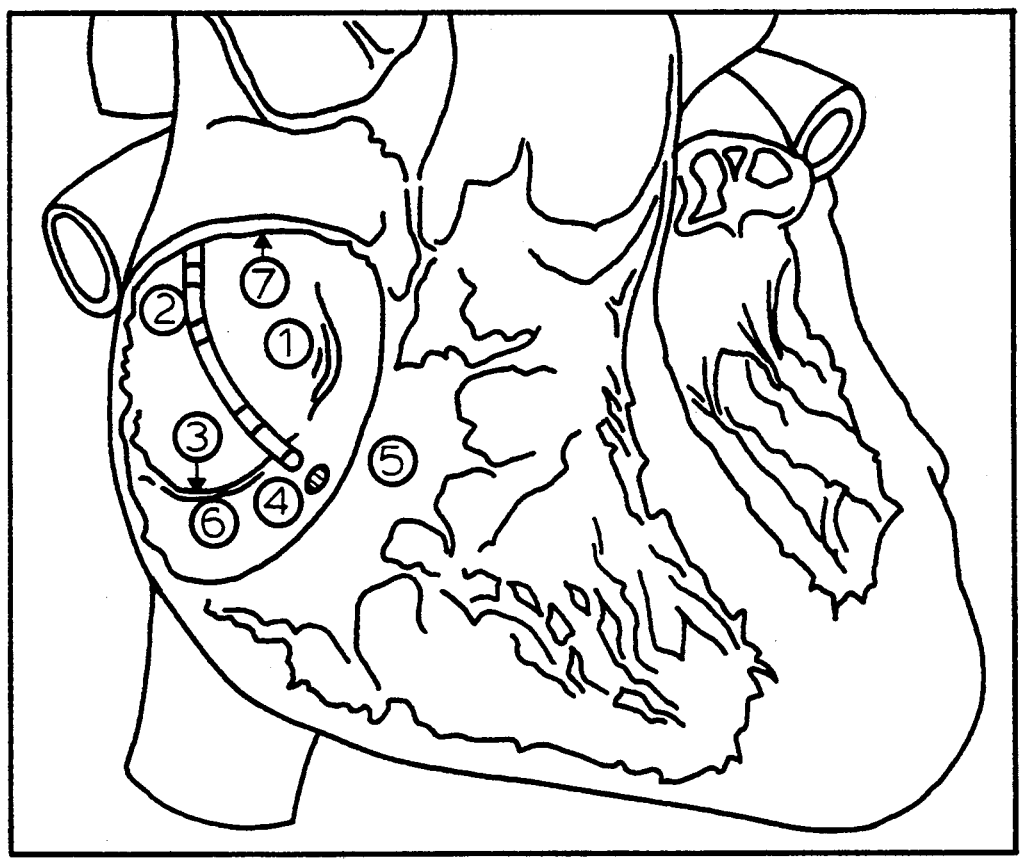
FIG. 1 is a cut away view of the human heart, Specifically the right atrium, illustrating the relative location, for example, of the inferior vena cava, fossa ovalis, superior vena cava, valve of the coronary sinus and the ostium of the coronary sinus.

To understand the use of such a catheter, it is first important to review the structure of the human heart as shown in FIG. 1. A typical human heart contains four chambers, a right and left atrium and right and left ventricle. The right atrium of the heart receives blood returning to the heart through the inferior vena cava and superior vena cava. Adjacent to the opening in the right atrium of the inferior vena cava is the ostium of the coronary sinus. A tissue fold or primative valve covers the coronary sinus ostium to prevent blood from backflowing into the coronary sinus as it is being pumped out of the right atrium. (Gray, Anatomy of the Human Body, 23rd. Ed. p. 527 (1936)) This coronary sinus ostium is a compliant semi-circular fold comprised of the lining membrane of the atrium. Within the right atrium generally and above the coronary sinus valve specifically is an oval depression called the fossa ovalis. Between the inferior vena cava and the coronary sinus ostium is also the eustaclan ridge. The precise location of each of these elements may vary from patient to patient.

One of the difficulties in performing procedures within the coronary sinus is finding the ostium to the coronary sinus while the heart is beating. As earlier stated, the opening or ostium of the coronary sinus is located in the right atrium between the tricuspid valve, the fossa ovalis and the inferior vena cava. Two approaches have been used for the placement of an electrophysiology catheter within the coronary sinus, an inferior approach from below the heart and a superior approach from above the heart. In the inferior approach a catheter, especially a steerable catheter, is advanced through the femoral vein into the right atrium. The tip of the catheter is then curved remotely to aim it toward the ostium of the coronary sinus. In the superior approach, a catheter is advanced through either the internal jugular or subclavian vein through the superior vena cava into the right atrium until it is directed toward the coronary sinus.

Gaining access to the ostium of the coronary sinus is a very difficult procedure. As previously discussed, there are a number of anatomical structures within the right atrium which can be easily confused with the coronary sinus. Further, these particular features of the heart do not show up well on a fluoroscope, thus making the procedure quite difficult and time consuming for the physician.

The catheter of the present invention is specifically configured to avoid these problems by its insertion through the superior vena cava into the right atrium to a position adjacent to the coronary sinus ostium. The catheter of the instant invention has a preformed curvature which permits it to be easily manipulated into the coronary sinus. In addition, the specific nature of the curve of the instant catheter permits important electrophysiological readings to occur while the catheter is within the coronary sinus, including analysis of both the right and left atrium and the left ventricle.

Figure 2:
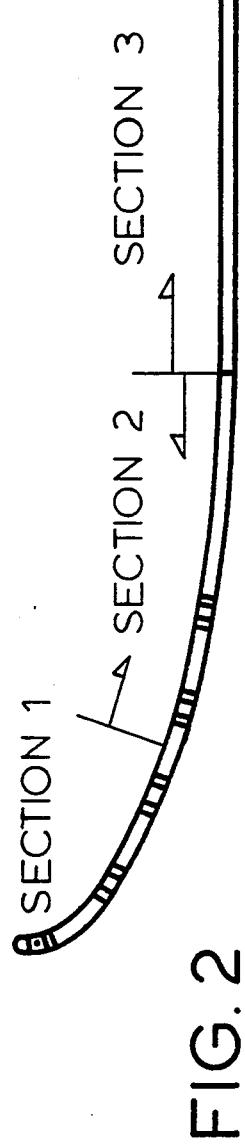
FIG. 2 is a side perspective drawing of the catheter.
Figure 3:
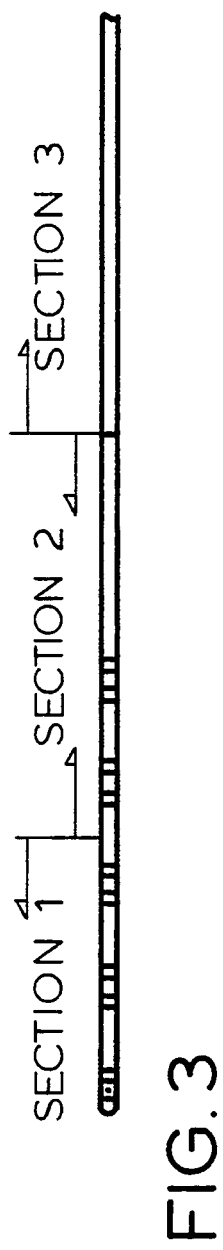
FIG. 3 is a front view of the catheter.

As shown in FIGS. 2 and 3, the catheter of the present invention has a distal end and a proximal end. It generally has three portions, a main reinforced portion, (Section 3) an intermediate zone portion (Section 2) and a softened tip portion(Section 1). See FIGS 2 and 3. The intermediate zone portion is more pliable than the main reinforced portion and the softened tip portion is more pliable than the intermediate zone portion. This increase in pliability can be achieved through conventional procedures well known in the industry. For example, the main reinforced portion can be formed of any conventional material having "memory" or permitting distortion from, and subsequent substantial return to, the desired shape. To reinforce this main reinforced portion, a reinforcing braid or other such suitable strand material having high tensile strength may be wound around the length of the main reinforced portion or incorporated into that portion of the catheter. Suitable reinforcing braid may be prepared from materials such as stainless steel, aramids sold under the trademark Kevlar ® by E.I. DuPont and nickel chromium alloys.

The intermediate zone portion is preferably formed of the same or a similar material with similar performance characteristics as is the reinforced zone portion but without addition of the reinforcing braid. The location of the merger of the reinforced section with the intermediate zone portion is not particularly critical. In a preferred embodiment, this junction is from about 7.0 to about 13.0 cm. and preferably from about 9.0 to about 11.0 cm. from the distal tip of the catheter. Distal from the intermediate zone is the softened tip portion which is more pliable than either the main reinforced portion or the intermediate zone portion. This enhanced pliability can be achieved by a number of methods well known in the industry and including use of a fused flexible tip catheters and soft tip catheters comprised of the same or similar materials with similar performance characteristics as are the reinforced and intermediate zone portions. Such tip designs are disclosed in U.S. Pat. Nos. 5,088,991, 4,596,563 and 5,078,702. In addition, a softened tip can be created through modifications made in the catheter such as additional drawing of the catheter body to reduce the thickness of the walls, thus achieving the enhanced pliability.

The relative length of the three zones are approximately 10.0 to about 130.0 cm. in length for the reinforced zone, about 5.0 to about 8.0 cm. in length for the intermediate zone and about 2.0 cm. to about 4.0 cm. in length for the softened tip portion. As will be discussed in more detail, although a preferred embodiment utilizes three zones of the catheter with varying degrees of rigidity, zones of the catheter with varying rigidity may be present. The essential element is the particular shape chosen for the catheter.

The curvature of the instant catheter contains two curves. After the extended straight portion of the catheter contained in the reinforced portion and a portion of the intermediate portion, the curvature begins within the intermediate zone of the catheter. This first preformed curvature is a longitudinal curve with a radius from about 7.0 cm. to about 11.0 cm., preferably from 8.0 cm. to about 10.00 cm. and most preferably about 9.0 cm. in length. This first curvature curves through an arch of about 30 to about 50 degrees, preferably from about 35 to about 45 degrees and most preferably about 40 degrees of arc. At the distal end of this first curve is a second longitudinal curve or "hook curve" with a radius from about 0.5 to about 2.0 cm., preferably from about 0.5 to about 1.5 cm. and most preferably about 1.0 cm. The second curve extends through an arc from about 45 to about 90 degrees, preferably from about 50 to about 70 degrees and most preferably about 60 degrees of arc. The second curve is an extension of the first curve, curving in the same direction as the first curve. Preferably, the first and second longitudinal curves are also substantially coplanar (within about 15 degrees of coplanar), though minor variations in the curve outside of the plane of the catheter are certainly within the confines of the invention. This second "hook curve" serves to partially limit the depth to which the distal end of the catheter can be inserted into the coronary sinus.

For the purpose of illustration and not limitation, the diameter of the catheter may vary from about 3.0 to about 8.0 "French" units (one "French" equals about one-third of a millimeter).

Toward the distal end of the catheter within a portion of the main reinforced portion, the intermediate zone portion and the softened tip portion may be placed a plurality of electrodes, preferably at least two with one of those at the tip. The number of electrodes and their placement on the body of the catheter will depend on the intended usage for the catheter. The ultimate number of electrodes may be as many as 10 or more electrodes. In one preferred embodiment, an electrode is placed both at the tip of the catheter and approximately where the first and second curves meet. By this placement, when the catheter of the instant invention is placed within the coronary sinus for sensing purposes, the catheter will be able to sense both sides of the coronary sinus at the same time.

The catheter of the instant invention preferably is divided into three portions: a main reinforced portion, (Section 3) an intermediate zone portion (Section 2) and a softened tip portion (Section 1). See FIGS. 2 and 3. However, catheters for a number of uses with the specific curvature but without the three distinct portions of the instant invention are also covered by this disclosure. The relative rigidity of the catheter throughout its length may not be particularly important as long as the desired curvature is present. Alternatively, the intended use for the catheter may be best accomplished by only two portions having different rigidity along the length of the catheter body. More frequent modifications of the rigidity of the catheter body than three may also be necessary, depending on the required use of the catheter.

If appropriate to the intended use, a lumen may also be incorporated into the catheter for infusion of fluids or withdrawal of blood samples. The diameter of the lumen should be sufficient to accomplish the intended use for the catheter. In this embodiment one or a plurality of vents would also be located near the distal tip of the catheter with the precise location and number depending on the intended use for the catheter.

In operation, a coronary sinus catheter as described in the instant invention containing electrodes from 2 to about 10 connected to electrophysiology sensing devices is inserted percutaneously through the internal jugular vein or the subclavian vein and advanced under fluoroscopic control through the superior vena cava to the right atrium. Insertion is also possible using the brachial vein or femoral vein approach. The coronary sinus catheter is then directed across the right atrium until it contacts the ostium of the coronary sinus. The particular structure and curvature of the instant coronary sinus catheter permits ease in locating the ostium of the coronary sinus. Under floroscopic guidance the catheter is advanced towards the tricuspid valve with the tip pointed medially. The tip of the coronary sinus catheter is then inserted within the coronary sinus and advanced as far as is required or desired. Continuous and stable recordings of the electrical pathways running near the coronary sinus can then be produced. As a result of the unique curvature of the coronary sinus catheter, as well as the unique structure of that catheter, it is relatively easy to locate the ostium of the coronary sinus and, in addition, take electrophysiology readings within the coronary sinus. In this fashion the time and x-ray exposure required during the procedure can be reduced.

In addition to the use for the coronary sinus catheter as a diagnostic electrophysiology catheter, it may also be used for other medical procedures within the coronary sinus. For example, by modifying the mode of the catheter, the types of medical instruments to which the proximal end of the catheter is attached, and the electrodes, the catheter can also serve as a means for interventional pacing or permanent pacing of the heart. Pacing using the coronary sinus catheter will also provide the ability to pace the left atrium. By the administration of a controlled amount of electrical energy to the heart, which is at that time experiencing an arrhythmia, the coronary sinus catheter may also be used for defibrillation purposes or for cardioversion. The catheter may also be utilized for permanent implantable pacing by various modifications to the catheter. For this application the material used to manufacture the catheter may be modified to better adapt to long-term invasive medical procedures. For example, when the catheter functions as a permanent pacing catheter lead, the structure of the catheter may not contain braided portions which might interfere with the pacing procedures. Further, the shape, size and placement of the electrodes on the catheter may also be modified for the specialized procedure. Other uses well known in the industry are also contained within the description of the invention.

While it is apparent from the foregoing that particular forms of the invention have been illustrated and described, various modifications can be made without departing from the spirit and scope of the invention. Accordingly, it is not intended that the invention be limited except by the appended claims.

We claim:

1. A catheter for use in the coronary sinus comprising an elongated member having a main reinforced portion, an intermediate zone portion and a tip portion, wherein said main reinforced portion is reinforced by a strand means for reinforcing said main reinforced portion, wherein the intermediate zone portion is constructed of conventional catheter materials, and wherein the tip portion is constructed more pliable than the intermediate zone portion, using conventional catheter construction procedures and wherein a portion of the catheter is curved in a first and second curve, wherein the first curve is a first longitudinal curve with a radius from about 7.0 cm. to about 11.0 cm. with the radius extending through an arc of about 30 to about 50 degrees, wherein the second curve is a second longitudinal curve with a radius of about 0.5 cm. to about 2.0 cm. which radius extends through an arc of about 45 to about 90 degrees, wherein the second longitudinal curve is curved in the same direction as the first longitudinal curve, and wherein the first and second longitudinal curves are substantially coplanar.

2. The catheter of claim 1 wherein the first longitudinal curve has a radius from about 8.0 to about 10.0 cm. with the radius extending from about 35 to about 45 degrees of arc.

3. The catheter of claim 1 wherein the first longitudinal curve has a radius from about 8.0 to about 10.0 cm. with the radius extending at about 40 degrees of arc.

4. The catheter of claim 1 wherein the second curve has a radius of about 0.5 cm. to about 1.5 cm. with the radius extending through an arc of about 50 to about 70 degrees.

5. The catheter of claim 1 wherein the second curve has a radius of about 0.5 cm. to about 1.5 cm. with the radius extending through an arc of about 60 degrees.

6. The catheter of claim 1 wherein the elongated member includes a lumen and a plurality of vents, wherein said vents are located near a distal tip of the member.

7. A catheter for use in the coronary sinus for specialized medical procedures comprising an elongated member having a main reinforced portion, an intermediate zone portion and a tip portion, wherein said main reinforced portion is reinforced by wire braid, wherein the intermediate zone portion is constructed of conventional catheter material, wherein the tip portion is constructed more pliable than the intermediate zone portion by conventional catheter construction procedures, wherein said tip portion is tapered, wherein a portion of the main reinforced portion, all of the intermediate zone portion and the tip portion are curved in a compound curve, wherein a first portion of the compound curve is a first longitudinal curve with a radius of about 7.0 cm. to about 11.0 cm. with a radius extending through an arc of about 30 to about 50 degrees of arc, wherein a second portion of the compound curve is a second longitudinal curve with a radius of about 0.5 to about 2.0 cm. which radius extends through an arc of about 45 to about 90 degrees, wherein the second longitudinal curve is curved in the same direction as the first longitudinal curve, and wherein the first and second longitudinal curve are substantially coplanar.

8. The catheter of claim 7 wherein the first longitudinal curve has a radius from about 8.0 to about 10.0 cm. with the radius extending from about 35 to about 45 degrees of arc.

9. The catheter of claim 7 wherein the first longitudinal curve has a radius from about 8.0 to about 10.0 cm. with the radius extending from about 40 degrees of arc.

10. The catheter of claim 7 wherein the second curve has a radius of about 0.5 cm. to about 1.5 cm. with the radius extending through an arc of about 50 to about 70 degrees.

11. The catheter of claim 7 wherein the second curve has a radius of about 0.5 cm. to about 1.5 cm. with the radius extending through an arc of about 60 degrees.

12. A catheter for use in a coronary sinus comprising an elongated member, wherein a portion of the member is curved in a first and second curve, wherein the first curve is a first longitudinal curve with a radius from about 7.0 cm. to about 11.0 cm. with a radius extending through an arc of about 30 to about 50 degrees, wherein the second curve is a second longitudinal curve with a radius of about 0.5 cm. to about 2.0 cm. which radius extends through an arc of about 45 to about 90 degrees, wherein the second longitudinal curve is curved in the same direction as the first longitudinal curve, and wherein the first and second longitudinal curves are substantially coplanar.

13. The catheter of claim 12 wherein the elongated member includes a lumen and a plurality of vents, wherein said vents are located near a distal tip of the member.

* * * * *